United States Patent [19]

Ladduwahetty et al.

[11] Patent Number: 5,710,161

[45] Date of Patent: Jan. 20, 1998

[54] TRIAZOLE DERIVATIVES AND THEIR USE AS THERAPEUTIC AGENTS

[75] Inventors: Tamara Ladduwahetty, London; Angus Murray MacLeod, Bishops Stortford, both of United Kingdom

[73] Assignee: Merck, Sharp & Dohme, Ltd., Hoddesdon, England

[21] Appl. No.: 527,280

[22] Filed: Sep. 12, 1995

[30] Foreign Application Priority Data

Sep. 15, 1994 [GB] United Kingdom ............... 9418545

[51] Int. Cl.$^6$ .............. A61K 31/445; C07D 401/06; C07D 401/14
[52] U.S. Cl. ................................ 514/278; 546/17
[58] Field of Search ............................ 546/17; 514/278

[56] References Cited

U.S. PATENT DOCUMENTS 5,411,980   5/1995   Ashton et al. ...................... 548/263.2

FOREIGN PATENT DOCUMENTS 0 323 737 A1   7/1989   European Pat. Off. .
394 989 A3    10/1990   European Pat. Off. .
436 334 A3     7/1991   European Pat. Off. .

OTHER PUBLICATIONS

Malbec, F. et al. "Derivatives of 2,4-dihydro-1,2,4-triazole-3-thione and 2-amino-1,3,4-thiadiazole from thiosemicarbazones of esters" Chemical Abstracts, vol. 103, No. 22, Jul. 22, 1985, PG. 571, COL. 1, Abstract No. 22 524w.

Khripak, S. M. et al. "Acylation and iodination of 5-p-phenyl-1,2, 4-triazole-3-thiones" Chemical Abstracts, vol. 101, No. 25, Dec. 17, 1984, p. 761, COL. 1, Abstract No. 230 418 a.

Knysh, E. G. et al. "Synthesis and properties of 5-heteroarylthio-1, 2,-4triazoles" Chemical Abstracts, vol. 105, No. 8, Sep. 1, 1986, p. 17, COL. 1, Abstract No. 72 087t.

Knish, E. G. et al. "Synthesis, properties and biological activity of 5-(acylalkylthio)-1,2,4-triazoles" Chemical Abstracts, vol. 99, No. 8, Aug. 1, 1983, p. 521, COL. 2, Abstract No. 38 421v.

S. L. Ramnarine et al. "Sensory-Efferent Neural Control of Mucus Secretion: Characterization Using Tachykinin Receptor Antagonists in Ferret Trachea in Vitro" Br. J. Pharmacol. (1994) 113, 1183–1190.

*Primary Examiner*—Patricia L. Morris
*Attorney, Agent, or Firm*—Robert J. North; Melvin Winokur

[57] ABSTRACT

The present invention relates to compounds of the formula (I):

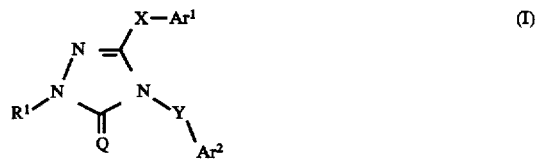

wherein $Ar^1$ represents optionally substituted phenyl;

$Ar^2$ represents aryl; benzhydryl; or benzyl; wherein each aryl and heteroaryl and each phenyl moiety of benzyl and benzhydryl may be substituted;

$R^1$ represents H or a group of the formula $Z$-$R^2$;

$R^2$ represents H, $CO_2R^7$, $CONR^7R^8$, $NR^7R^8$, $NR^7COR^9$, $NR^7SO_2R^8$, trifluoromethyl, heteroaryl or —O-heteroaryl, each of which heteroaryl groups are as previously defined and may be optionally substituted, or $R^2$ represents a group selected from phenyl, piperazinyl, piperidinyl, spiro-fused piperidinyl, tetrahydroquinolinyl or tetrahydroisoquinolinyl, each of which may be substituted;

$R^3$, $R^4$, $R^5$ and $R^6$ each independently represent H or $C_{1-4}$alkyl;

$R^7$ and $R^8$ each independently represent H, $C_{1-6}$alkyl, trifluoromethyl, phenyl or benzyl;

Q represents O or S;

X represents a group selected from —$CR^3R^4CR^5R^6$-, —$CR^3$=$CR^4$—, —$C(OH)R^3CR^4R^5$-, —$CR^3R^4C(OH)R^5$-, —$C(O)CR^3R^4$- and —$CR^3R^4C(O)$—;

Y represents a $C_{1-4}$alkylene chain; and

Z represents a straight or branched $C_{1-6}$alkylene or $C_{3-6}$alkenylene chain with the proviso that the alkenylene double bond does not terminate at a carbon atom attached to a nitrogen atom;

and pharmaceutically acceptable salts thereof.

The compounds are of particular use in the treatment or prevention of pain, inflammation, emesis and postherpetic neuralgia.

12 Claims, No Drawings

TRIAZOLE DERIVATIVES AND THEIR USE AS THERAPEUTIC AGENTS

This invention relates to a class of aromatic compounds, which are useful as tachykinin antagonists. More particularly, the compounds of the invention comprise a substituted triazolyl ring system.

The tachykinins are a group of naturally occurring peptides found widely distributed throughout mammalian tissues, both within the central nervous system and in peripheral nervous and circulatory systems.

The tachykinins are distinguished by a conserved carboxyl-terminal sequence:

At present, there are three known mammalian tachykinins referred to as substance P, neurokinin A (NKA, substance K, neuromedin L) and neurokinin B (NKB, neuromedin K) (for review see J. E. Maggio, *Peptides* (1985) 6(suppl. 3), 237–242). The current nomenclature designates the three tachykinin receptors mediating the biological actions of substance P, NKA and NKB as the $NK_1$, $NK_2$ and $NK_3$ receptors, respectively.

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases, proliferative vitreoretinopathy, irritable bowel syndrome and disorders of bladder function including cystitis and bladder detruser hyper-reflexia is reviewed in "Tachykinin Receptors and Tachykinin Receptor Antagonists", C. A. Maggi, R. Patacchini, P. Rovero and A. Giachetti, *J. Auton. Pharmacol.* (1993) 13, 23–93.

For instance, substance P is believed inter alia to be involved in the neurotransmission of pain sensations (Otsuka et al, "Role of Substance P as a Sensory Transmitter in Spinal Cord and Sympathetic Ganglia" in 1982 *Substance P in the Nervous System*, Ciba Foundation Symposium 91, 13–34 (published by Pitman) and Otsuka and Yanagisawa, "Does Substance P Act as a Pain Transmitter?" *TIPS* (1987) 8, 506–510), specifically in the transmission of pain in migraine (Sandberg et al, *J. Med. Chem.*, (1982) 25, 1009) and in arthritis (Levine et al in *Science* (1984) 226, 547–549). Tachykinins have also been implicated in gastrointestinal (GI) disorders and diseases of the GI tract such as inflammatory bowel disease (Mantyh et al in *Neuroscience* (1988) 25(3), 817–837 and D. Regoli in "Trends in Cluster Headache" Ed. Sicuteri et al, Elsevier Scientific Publishers, Amsterdam (1987) page 85–95) and emesis (F. D. Tattersall et al, *Eur. J. Pharmacol.*, (1993) 250, R5–R6). It is also hypothesised that there is a neurogenic mechanism for arthritis in which substance P may play a role (Kidd et al "A Neurogenic Mechanism for Symmetrical Arthritis" in *The Lancet*, 11 Nov. 1989 and Grönblad et al, "Neuropeptides in Synovium of Patients with Rheumatoid Arthritis and Osteoarthritis" in *J. Rheumatol.* (1988) 15(12), 1807–1810). Therefore, substance P is believed to be involved in the inflammatory response in diseases such as rheumatoid arthritis and osteoarthritis, and fibrositis (O'Byrne et al, *Arthritis and Rheumatism* (1990) 33, 1023–1028). Substance P antagonists alone or in combination with bradykinin receptor antagonists may also be useful in the prevention and treatment of inflammatory conditions in the lower urinary tract, especially cystitis (Giuliani et al, *J. Urology* (1993) 150, 1014–1017). Other disease areas where tachykinin antagonists are believed to be useful are allergic conditions (Hamelet et al, *Can. J. Pharmacol. Physiol.* (1988) 66, 1361–1367), immunoregulation (Lotz et al, *Science* (1988) 241, 1218–1221; Kimball et al, *J. Immunol.* (1988) 141(10), 3564–3569 and Perianin et al, *Biochem. Biophys. Res. Commun.* (1989) 161, 520), post-operative pain and nausea (Bountra et al, *Eur. J. Pharmacol.* (1993) 249, R3–R4 and Tattersall et al, *Neuropharmacology* (1994) 33, 259–260), vasodilation, bronchospasm, reflex or neuronal control of the viscera (Mantyh et al, *PNAS* (1988) 85, 3235–3239) and, possibly by arresting or slowing β-amyloid-mediated neurodegenerative changes (Yankner et al, *Science* (1990) 250, 279–282) in senile dementia of the Alzheimer type, Alzheimer's disease and Down's Syndrome.

Tachykinin antagonists may also be useful in the treatment of small cell carcinomas, in particular small cell lung cancer (SCLC) (Langdon et al, *Cancer Research* (1992) 52, 4554–7).

Substance P may also play a role in demyelinating diseases such as multiple sclerosis and amyotrophic lateral sclerosis (Luber-Narod et al, poster C.I.N.P. XVIIIth Congress, 28th Jun.–2nd Jul. 1992), and in disorders of bladder function such as bladder detrusor hyper-reflexia (*The Lancet*, 16th May 1992, 1239). Antagonists selective for the NK-1 and/or NK-2 receptor may be useful in the treatment of asthmatic disease (Frossard et al, *Life Sci.* (1991) 49, 1941–1953; Advenier et al, *Biochem. Biophys. Res. Commun.* (1992) 184(3), 1418–1424; and Barnes et al, *TIPS* (1993) 11, 185–189).

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophilic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosus (European patent specification no. 0 436 334), ophthalmic disease such as conjuctivitis, vernal conjunctivitis, and the like, and cutaneous diseases such as contact dermatitis, atopic dermatitis, urticaria, and other eczematoid dermatitis (European patent specification no. 0 394 989).

Substance P antagonists may also be useful in mediating neurogenic mucus secretion in mammalian airways and hence provide treatment and symptomatic relief in diseases characterized by mucus secretion, in particular, cystic fibrosis (see Ramnarine et al, abstract presented at 1993 ALA/ ATS International Conference, 16–19 May 1993, published in *Am. Rev. Resp. Dis.* (May 1993)).

In view of their metabolic instability, peptide derivatives are likely to be of limited utility as therapeutic agents. It is for this reason that non-peptide tachykinin antagonists are sought.

In essence, this invention provides a class of potent non-peptide tachykinin antagonists.

The present invention provides a compound of the formula (I) or a pharmaceutically acceptable salt thereof:

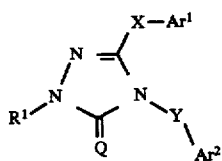
(I)

wherein Ar¹ represents phenyl optionally substituted by 1, 2 or 3 groups selected from $C_{1-6}$alkyl, $C_{2-6}$alkenyl, $C_{2-6}$alkynyl, $C_{3-7}$cycloalkyl, $C_{3-7}$cycloalkyl$C_{1-4}$alkyl, halo, cyano, nitro, trifluoromethyl, trimethylsilyl, —OR$^a$, —SR$^a$, —SOR$^a$, —SO$_2$R$^a$, —NR$^a$R$^b$, —NR$^a$COR$^b$, —NR$^a$CO$_2$R$^b$, —COR$^a$, —CO$_2$R$^a$ or —CONR$^a$R$^b$, where R$^a$ and R$^b$ each independently represent H, $C_{1-6}$alkyl, phenyl or trifluoromethyl;

Ar² represents aryl selected from phenyl and naphthyl; heteroaryl selected from indolyl, indazolyl, thienyl, furyl, pyridyl, thiazolyl, triazolyl, tetrazolyl and quinolyl; benzhydryl; or benzyl; wherein each aryl and heteroaryl and each phenyl moiety of benzyl and benzhydryl may be substituted by 1, 2 or 3 groups selected from $C_{1-6}$alkyl, $C_{1-6}$alkoxy, $CO_2C_{1-4}$alkyl, cyano, halo and trifluoromethyl;

R¹ represents H or a group of the formula Z-R²;

R² represents H, CO$_2$R$^7$, CONR$^7$R$^8$, NR$^7$R$^8$, NR$^7$COR$^9$, NR$^7$SO$_2$R$^8$, trifluoromethyl, heteroaryl or —O-heteroaryl, each of which heteroaryl groups are as previously defined and may be optionally substituted by $C_{1-6}$alkyl, $C_{1-6}$alkoxy, oxo, $CO_2C_{1-4}$alkyl, cyano, halo or trifluoromethyl, or R² represents a group of the formula (i) to (vi):

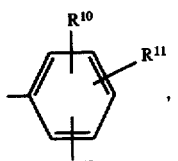
(i)

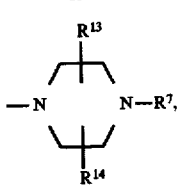
(ii)

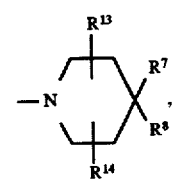
(iii)

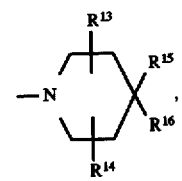
(iv)

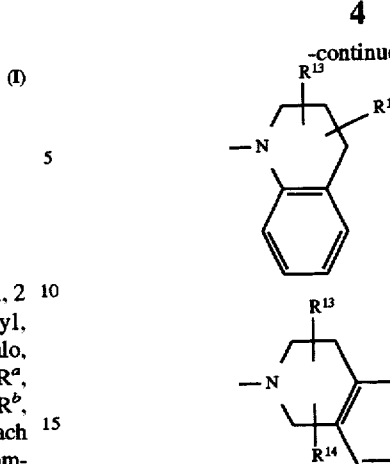
(v)

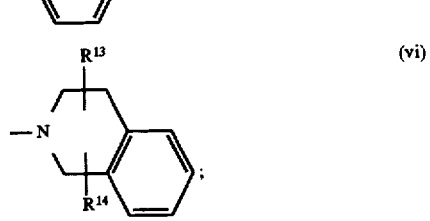
(vi)

R³, R⁴, R⁵ and R⁶ each independently represent H or $C_{1-4}$alkyl;

R⁷ and R⁸ each independently represent H, $C_{1-6}$alkyl, trifluoromethyl, phenyl or benzyl;

R⁹ represents H, $C_{1-6}$alkyl, trifluoromethyl, phenyl, benzyl, or $C_{1-4}$alkyl substituted by an optionally substituted heteroaryl group as previously defined;

R¹⁰ and R¹¹ each independently represent H, halo, $C_{1-6}$alkyl, $C_{1-6}$alkoxy, $CO_2C_{1-4}$alkyl, trifluoromethyl or cyano;

R¹² represents H, halo, $C_{1-6}$alkyl, $C_{1-6}$alkoxy, $CO_2C_{1-4}$alkyl, trifluoromethyl, cyano, NR$^7$COR$^{17}$, NR$^7$SO$_2$R$^8$, or NR$^7$R$^{17}$;

R¹³ and R¹⁴ each independently represent H or $C_{1-6}$alkyl;

R¹⁵ and R¹⁶ together form a 5- or 6-membered non-aromatic ring which may contain one NR$^{18}$ group, which ring may be substituted by or have fused thereto a phenyl group optionally substituted by 1 or 2 groups selected from halo, $C_{1-6}$alkyl, $C_{2-6}$alkenyl, $C_{1-6}$alkoxy, $CO_2C_{1-4}$alkyl, trifluoromethyl and cyano;

R¹⁷ represents H, $C_{1-6}$alkyl, trifluoromethyl, phenyl, benzyl or indolyl, wherein each phenyl, benzyl or indolyl substituent may be optionally substituted by 1, 2 or 3 groups selected from $C_{1-6}$alkyl, $C_{1-6}$alkoxy, $CO_2C_{1-4}$alkyl, halo, trifluoromethyl and cyano;

R¹⁸ represents H, CO$_2$R$^{19}$, CONR$^7$R$^8$, SONR$^7$R$^8$ or SO$_2$R$^{19}$;

R¹⁹ represents $C_{1-6}$alkyl, phenyl or benzyl;

Q represents O or S;

X represents a group selected from —CR³R⁴CR⁵R⁶-, —CR³=CR⁴—, —C(OH)R³CR⁴R⁵-, —CR³R⁴C(OH)R⁵-, —C(O)CR³R⁴- and —CR³R⁴C(O)—;

Y represents a $C_{1-4}$alkylene chain; and

Z represents a straight or branched $C_{1-6}$alkylene or $C_{3-6}$alkenylene chain with the proviso that the alkenylene double bond does not terminate at a carbon atom attached to a nitrogen atom.

As used herein, the definition of each expression, when it occurs more than once in any structure, is intended to be independent of its definition elsewhere in the same structure.

The alkyl, alkenyl and alkynyl groups referred to with respect to the formulae herein may represent straight or branched groups, or combinations thereof. Thus, for example, suitable alkyl groups include methyl, ethyl, n- or iso-propyl, n-, sec-, iso- or tert-butyl.

The term cycloalkyl referred to with respect to the definitions herein may represent, for example, cyclopropyl, cyclobutyl, cyclopentyl or cyclohexyl. Similarly cycloalkylalkyl groups may be, for example, cyclopropylmethyl.

Suitable alkenyl groups include vinyl and allyl; and suitable alkynyl groups include propargyl.

The term "halo" as used herein includes fluoro, chloro, bromo and iodo, especially chloro and fluoro.

Those compounds according to the invention which contain one or more chiral centres may exist both as enantiomers and as diastereomers. It is to be understood that all such isomers and mixtures thereof are encompassed within the scope of the present invention.

Preferably $Ar^1$ represents substituted phenyl. When $Ar^1$ is substituted phenyl suitable substituents include nitro, trifluoromethyl, trimethylsilyl, bromo, chloro, fluoro, iodo, cyano, methyl, ethyl, cyclopropyl, t-butyl, vinyl, methoxy, phenoxy, amino and carbonylmethoxy. Preferably $Ar^1$ represents phenyl substituted by one or more groups selected from $C_{1-6}$alkyl such as methyl and t-butyl, halo such as chloro, fluoro and bromo, and trifluoromethyl.

Preferably $Ar^1$ represents disubstituted phenyl, in particular 3,5-disubstituted phenyl, for example 3,5-disubstituted phenyl wherein the substituents are selected from $C_{1-6}$alkyl, halo and trifluoromethyl. More preferably $Ar^1$ represents 3,5-bis(trifluoromethyl)phenyl.

Preferably $Ar^2$ represents unsubstituted or substituted phenyl, most preferably unsubstituted phenyl.

Preferably, Q is O.

Preferably X represents —$CR^3R^4CR^5R^6$—, most preferably where $R^3$, $R^4$, $R^5$ and $R^6$ each independently represent H.

Preferably Z represents a $C_{1-4}$alkylene chain, especially —$CH_2$—, —$CH_2$—$CH_2$— or —$(CH_2)_3$—;

Preferably $R^2$ represents a group selected from $CO_2R^7$ where $R^7$ represents $C_{1-6}$alkyl, especially methyl; $NR^7COR^9$ where $R^7$ represents H and $R^9$ represents $C_{1-4}$alkyl, especially methyl, substituted by indolyl; heteroaryl, especially triazolyl; —O-heteroaryl, especially —O-pyridyl; or a group of formula (i) where $R^{10}$ and $R^{11}$ each preferably represent H or halo, especially chloro, and $R^{12}$ preferably represents H, or $NR^7R^{17}$ where $R^7$ and $R^{17}$ are as previously defined, especially where $R^7$ represents H or $C_{1-6}$alkyl and $R^{17}$ represents benzyl optionally substituted by 1 or 2 halo atoms, especially chlorine atoms; or a group of formula (ii) where $R^7$ preferably represents $C_{1-6}$alkyl, especially methyl, and $R^{13}$ and $R^{14}$ are preferably both H; or a group of formula (iii) where $R^7$ preferably represents H, phenyl or benzyl, and $R^8$, $R^{13}$ and $R^{14}$ are each preferably H; or a group of formula (iv) where $R^{13}$ and $R^{14}$ are preferably both H and $R^{15}$ and $R^{16}$ together form a 5-membered non-aromatic ring optionally containing one $NR^{18}$ group, preferably where $R^{18}$ is $SO_2R^{19}$ and $R^{19}$ is $C_{1-6}$alkyl, especially methyl, to which ring is fused a phenyl group; or a group of formula (v) where $R^{13}$ and $R^{14}$ are preferably both H; or a group of formula (vi) where $R^{13}$ and $R^{14}$ are preferably both H.

It will be appreciated that, when a heterocyclic moiety is substituted by an oxo substituent, different tautomeric forms are possible so that the substituent may be represented as =O or —OH. For the avoidance of doubt, all such tautomeric forms are embraced by the present invention.

A particularly suitable sub-class of compounds of the formula (I) are those of formula (Ia) and salts thereof:

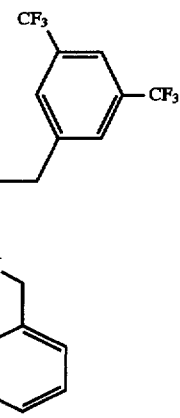
(Ia)

wherein $R^2$ and Z are as defined for formula (I).

Specific compounds within the scope of the invention include:

3-(3,5-bis(trifluoromethyl)phenethyl)-4-benzyl-1-(3-(4-phenylpiperidino)propyl)-5-oxo-1,2,4-triazole;

3-(3,5-bis(trifluoromethyl)phenethyl)-4-benzyl-1-(3-(4-benzylpiperidino)propyl)-5-oxo-1,2,4-triazole;

3-(3,5-bis(trifluoromethyl)phenethyl)-4-benzyl-1-(3-(1,2,3,4-tetrahydroisoquinolin-2-yl)propyl)-5-oxo-1,2,4-triazole;

and pharmaceutically acceptable acid addition salts thereof.

For use in medicine, the salts of the compounds of formula (I) will be pharmaceutically acceptable salts. Other salts may, however, be useful in the preparation of the compounds according to the invention (such as the dibenzoyltartrate salts) or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable non-toxic acid such as hydrochloric acid, sulphuric acid, fumaric acid, maleic acid, succinic acid, acetic acid, citric acid, tartaric acid, carbonic acid, phosphoric acid or p-toluenesulphonic acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

Preferred salts of the compounds according to the invention include the hydrochloride and p-toluenesulphonic acid salts.

The invention also provides pharmaceutical compositions comprising one or more compounds of this invention in association with a pharmaceutically acceptable carrier. Preferably these compositions are in unit dosage forms such as tablets, pills, capsules, powders, granules, solutions or suspensions, or suppositories, for oral, parenteral or rectal administration, or topical administration including administration by inhalation or insufflation.

The invention further provides a process for the preparation of a pharmaceutical composition comprising a compound of formula (I), or a salt or prodrug thereof, and a pharmaceutically acceptable carrier, which process comprises bringing a compound of formula (I), or a salt or prodrug thereof into association with a pharmaceutically acceptable carrier.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Preferred compositions for administration by injection include those comprising a compound of formula (I), as the active ingredient, in association with a surface-active agent (or wetting agent or surfactant) or in the form of an emulsion (as a water-in-off or off-in-water emulsion).

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion will preferably comprise fat droplets between 0.1 and 1.0 µm, particularly 0.1 and 0.5 µm, and have a pH in the range of 5.5 to 8.0.

Particularly preferred emulsion compositions are those prepared by mixing a compound of formula (I) with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The present invention futher provides a process for the preparation of a pharmaceutical composition comprising a compound of formula (I), which process comprises bringing a compound of formula (I) into association with a pharmaceutically acceptable carrier or excipient.

The compounds of formula (I) are of value in the treatment of a wide variety of clinical conditions which are characterised by the presence of an excess of tachykinin, in particular substance P, activity. These may include disorders of the central nervous system such as anxiety, depression, psychosis and schizophrenia; epilepsy; neurodegenerative disorders such as dementia, including AIDS related dementia, senile dementia of the Alzheimer type, Alzheimer's disease and Down's syndrome; demyelinating diseases such as multiple sclerosis (MS) and amyotrophic lateral sclerosis (ALS; Lou Gehrig's disease) and other neuropathological disorders such as peripheral neuropathy, for example AIDS related neuropathy, diabetic and chemotherapy-induced neuropathy, and postherpetic and other neuralgias; neuronal damage, such as cerebralschemic damage and cerebral edema in cerebrovascular disorders; small cell carcinomas such as small cell lung cancer; respiratory diseases, particularly those associated with excess mucus secretion such as chronic obstructive airways disease, bronchopneumonia, chronic bronchitis, asthma, and bronchospasm; airways diseases modulated by neurogenic inflammation; diseases characterised by neurogenic mucus secretion, such as cystic fibrosis; diseases associated with decreased glandular secretions, including lacrimation, such as Sjogren's syndrome, hyperlipoproteinemias IV and V, hemocromatosis, sarcoidosis, and amyloidosis; inflammatory diseases such as inflammatory bowel disease, psoriasis, fibrositis, ocular inflammation, osteoarthritis, rheumatoid arthritis, pruritis and sunburn; allergies such as eczema and rhinitis; hypersensitivity disorders such as poison ivy; ophthalmic diseases such as conjunctivitis, vernal conjunctivitis, dry eye syndrome, and the like; ophthalmic conditions associated with cell proliferation such as proliferative vitreoretinopathy; cutaneous diseases such as contact dermatitis, atopic dermatitis, urticaria, and other eczematoid dermatitis; addiction disorders including the withdrawal response produced by chronic treatment with, or abuse of, drugs such as benzodiazepines, opiates, cocaine, alcohol and nicotine; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosus; gastrointestinal (GI) disorders, including inflammatory disorders and diseases of the GI tract such as gastritis, gastroduodenal ulcers, gastric carcinomas, gastric lymphomas, disorders associated with the neuronal control of viscera, ulcerative colitis, Crohn's disease, irritable bowel syndrome and emesis, including acute, delayed, post-operative, late phase or anticipatory emesis such as emesis induced by chemotherapy, radiation, toxins, viral or bacterial infections, pregnancy, vestibular disorders, motion, surgery, migraine, opioid analgesics, and variations in intercranial pressure, in particular, for example, drug or radiation induced emesis or post-operative nausea and vomiting; disorders of bladder function such as cystitis, bladder detrusor hyper-reflexia and incontinence; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions, especially the transmission of pain in migraine.

Hence, the compounds of the present invention may be of use in the treatment of physiological disorders associated with excessive stimulation of tachykinin receptors, especially neurokinin-1 receptors, and as neurokinin-1 antagonists for the control and/or treatment of any of the aforementioned clinical conditions in mammals, including humans.

The compounds of formula (I) are also of value in the treatment of a combination of the above conditions, in particular in the treatment of combined post-operative pain and post-operative nausea and vomiting.

The compounds of formula (I) are particularly useful in the treatment of emesis, including acute, delayed, post-operative, late phase or anticipatory emesis, such as emesis or nausea induced by chemotherapy, radiation, toxins, such as metabolic or microbial toxins, viral or bacterial infections, pregnancy, vestibular disorders, motion, mechanical stimulation, gastrointestinal obstruction, reduced gatrointestinal motility, visceral pain, psychological stress or disturbance, high altitude, weightlessness, opioid analgesics, intoxication, resulting for example from consumption of alcohol, surgery, migraine, and variations in intercranial pressure. Most especially, the compounds of formula (I) are of use in the treatment of emesis induced by antineoplastic (cytotoxic) agents including those routinely used in cancer chemotherapy.

Examples of such chemotherapeutic agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; and cytotoxic antibiotics.

Particular examples of chemotherapeutic agents are described, for instance, by D. J. Stewart in "*Nausea and Vomiting: Recent Research and Clinical Advances*", Eds. J. Kuucharczyk et al, CRC Press Inc., Boca Raton, Fla., USA (1991) pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil [R. J. Gralla et al in *Cancer Treatment Reports* (1984) 68(1), 163–172].

The compounds of formula (I) are also of use in the treatment of emesis induced by radiation including radiation therapy such as in the treatment of cancer, or radiation sickness; and in the treatment of post-operative nausea and vomiting.

It will be appreciated that the compounds of formula (I) may be presented together with another therapeutic agent as a combined preparation for simultaneous, separate or sequential use for the relief of emesis. Such combined preparations may be, for example, in the form of a twin pack.

A further aspect of the present invention comprises the compounds of formula (I) in combination with a 5-HT$_3$ antagonist, such as ondansetron, granisetron or tropisetron, or other anti-emetic medicaments, for example, a dopamine antagonist such as metoclopramide or GABA$_B$ receptor agonists such as baclofen. Additionally, a compound of formula (I) may be administered in combination with an anti-inflammatory corticosteroid, such as dexamethasone, triamcinolone, triamcinolone acetonide, flunisolide, budesonide, or others such as those disclosed in U.S. Pat. Nos. 2,789,118, 2,990,401, 3,048,581, 3,126,375, 3,929,768, 3,996,359, 3,928,326 and 3,749,712. Dexamethasone (Decadron™) is particularly preferred. Furthermore, a compound of formula (I) may be administered in combination with a chemotherapeutic agent such as an alkylating agent, antimetabolite, mitotic inhibitor or cytotoxic antibiotic, as described above. In general, the currently available dosage forms of the known therapeutic agents for use in such combinations will be suitable.

When tested in the ferret model of cisplatin-induced emesis described by F. D. Tattersall et al, in *Eur. J. pharmacol.*, (1993) 250, R5–R6, the compounds of the present invention were found to attenuate the retching and vomiting induced by cisplatin.

The compounds of formula (I) are also particularly useful in the treatment of pain or nociception and/or inflammation and disorders associated therewith such as, for example, neuropathy, such as diabetic and chemotherapy-induced neuropathy, postherpetic and other neuralgias, asthma, osteroarthritis, rheumatoid arthritis, headache and especially migraine.

The present invention further provides a compound of formula (I) for use in therapy.

According to a further or alternative aspect, the present invention provides a compound of formula (I) for use in the manufacture of a medicament for the treatment of physiological disorders associated with an excess of tachykinins, especially substance P.

The present invention also provides a method for the the treatment or prevention of physiological disorders associated with an excess of tachykinins, especially substance P, which method comprises administration to a patient in need thereof of a tachykinin reducing amount of a compound of formula (I) or a composition comprising a compound of formula (I).

For the treatment of certain conditions it may be desirable to employ a compound according to the present invention in conjunction with another pharmacologically active agent. For example, for the treatment of respiratory diseases such as asthma, a compound of formula (I) may be used in conjunction with a bronchodilator, such as a $\beta_2$-adrenergic receptor antagonist or tachykinin antagonist which acts at NK-2 receptors. The compound of formula (I) and the bronchodilator may be administered to a patient simultaneously, sequentially or in combination.

Likewise, a compound of the present invention may be employed with a leukotriene antagonists, such as a leukotriene $D_4$ antagonist such as a compound selected from those disclosed in European patent specification nos. 0 480 717 and 0 604 114 and in U.S. Pat. Nos. 4,859,692 and 5,270, 324. This combination is particularly useful in the treatment of respiratory diseases such as asthma, chronic bronchitis and cough.

The present invention accordingly provides a method for the treatment of a respiratory disease, such as asthma, which method comprises administration to a patient in need thereof of an effective amount of a compound of formula (I) and an effective amount of a bronchodilator.

The present invention also provides a composition comprising a compound of formula (I), a bronchodilator, and a pharmaceutically acceptable carrier.

It will be appreciated that for the treatment or prevention of migraine, a compound of the present invention may be used in conjunction with other anti-migraine agents, such as ergotamines or 5-$HT_1$ agonists, especially sumatriptan.

Likewise, for the treatment of behavioural hyperalgesia, a compound of the present invention may be used in conjunction with an antagonist of N-methyl D-aspartate (NMDA), such as dizocilpine.

For the treatment or prevention of inflammatory conditions in the lower urinary tract, especially cystitis, a compound of the present invention may be used in conjunction with an antiinflammatory agent such as a bradykinin receptor antagonist.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day.

For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

In the treatment of emesis using an injectable formulation, a suitable dosage level is about 0.001 to 10 mg/kg per day, preferably about 0.005 to 5 mg/kg per day, and especially 0.01 to 1 mg/kg per day. The compounds may be administered on a regimen of 1 to 4 times per day, preferably once or twice per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

The compounds of the formula (I) may be prepared by a process which comprises reacting a compound of the formula (II)

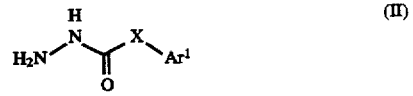
(II)

wherein X and $Ar^1$ are as defined for formula (I), with an isocyanate of the formula (III)

(III)

wherein Y and $Ar^2$ are as defined for formula (I); in the presence of base, followed by deprotection if required.

The reaction is conveniently carried out in a suitable organic solvent, such as dimethylformamide, at elevated temperature, such as in the region of 60° C. Favoured bases of use in the reaction include alkali metal hydroxides, such as sodium hydroxide.

Compounds of formula (I) may also be prepared from different compounds of formula (I) by interconversion processes. In particular, interconversion processes may be used to vary the group $R^1$. For example, compounds of formula (I) wherein $R^1$ is other than H may be prepared from the corresponding compounds of formula (I) wherein $R^1$ is H by conventional methods, such as reaction with a compound of the formula (IV)

(IV)

where $Hal^1$ and $Hal^2$ are halogen atoms, such as chlorine, bromine or iodine, and $Hal^1$ and $Hal^2$ are preferably different, for example, $Hal^1$ is chlorine and $Hal^2$ is iodine; followed by reaction with an amine of the formula $NHR^7R^8$ or a heteroaryl group as previously defined or a group of the formula V(a) to V(e):

(a)

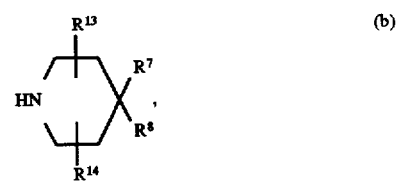
(b)

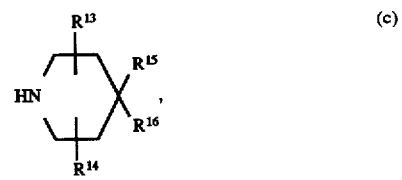
(c)

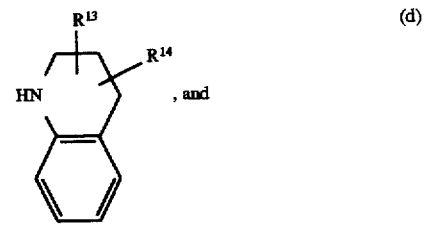
(d)

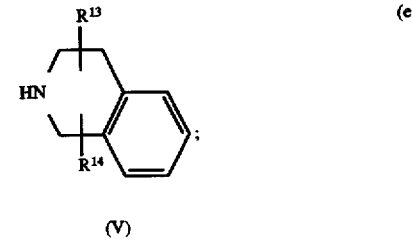
(e)

(V)

wherein $R^7$, $R^8$, $R^{13}$, $R^{14}$, $R^{15}$ and $R^{16}$ are as defined for formula (I).

The reaction with the dihalide of formula (IV) may be effected in a suitable organic solvent, such as dimethylformamide in the presence of a base such as an alkali metal hydride, for example, potassium hydride, preferably sodium hydride. Subsequent reaction with an amine of formula NHR$^7$R$^8$, a heteroaryl group or a compound of formula V(a) to V(e) may be effected in situ (without prior isolation of the intermediate) in the presence of a base such as potassium carbonate in a suitable organic solvent such as dimethylformamide, at elevated temperature such as in the region of 100° C.

Alternatively, compounds of formula (I) wherein R$^2$ is a group of the formula (i) as defined in relation to formula (I) may be prepared from the corresponding compounds of formula (I) wherein R$^1$ is H by reaction with a compound of formula (VI)

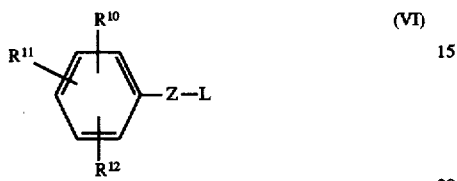

wherein R$^{10}$, R$^{11}$, R$^{12}$ and Z are as defined for formula (I) and L is a leaving group such as halo, for example chloro, bromo or iodo, or a sulphonate derivative, for example mesylate or tosylate; in the presence of a base, followed by deprotection if required.

The reaction is conveniently effected in a suitable organic solvent such as an ether, for example, 1,2-dimethoxyethane, at a temperature in the region of 0° C. Suitable bases of use in the reaction include alkali metal amides and hydrides, such as potassium bis(trimethylsilyl)amide or sodium hydride.

A particularly useful intermediate for the preparation of compounds of formula (I) wherein R$^{12}$ represents NR$^7$COR$^{17}$, NR$^7$SO$_2$R$^8$, or NR$^7$R$^{17}$ is the compound of formula (I) wherein R$^{12}$ represents NH$_2$. This compound may be prepared in a similar manner to that just described by the reaction of a compound of formula (I) wherein R$^1$ is H, with a compound of formula (VII)

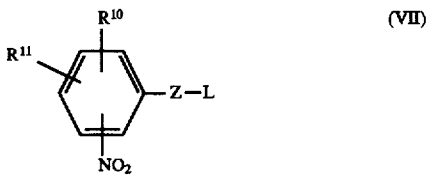

wherein R$^{10}$, R$^{11}$, Z and L are as previously defined; followed by reduction of the nitro group using, for example, catalytic hydrogenation in the presence of a catalyst such as platinum oxide or palladium on charcoal, to give the desired amine of formula (VIII)

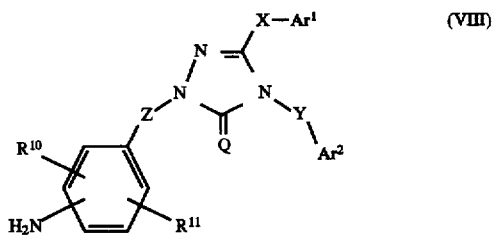

Compounds of formula (I) wherein R$^{12}$ represents NR$^7$COR$^{17}$ may be prepared by the reaction of a compound of formula (VIII) with a compound of the formula R$^{17}$COCl in the presence of a suitable acylation catalyst such as dimethylaminopyridine (DMAP). Similarly, compounds of formula (I) wherein R$^{12}$ represents NR$^7$SO$_2$R$^8$ may be prepared by the reaction of a compound of formula (VIII) with a compound of the formula R$^8$SO$_2$Cl in the presence of DMAP. Compounds of formula (I) wherein R$^{12}$ represents NR$^7$R$^{17}$ and R$^7$ and/or R$^{17}$ is/are other than H may be prepared by conventional methods, for example, by reductive amination involving the reaction of a compound of formula (VIII) and a compound of the formula RCHO (wherein R is, for instance C$_{1-5}$alkyl or phenyl) or a corresponding anhydride, followed by reduction using, for example, borane or a borohydride such as sodium cyanoborohydride.

Intermediates of formula (II) may be prepared from corresponding compounds of formula (IX):

wherein X and Ar$^1$ are as defined for formula (II), by reaction with hydrazine (NH$_2$NH$_2$). The reaction is conveniently effected in a suitable solvent such as an alcohol, for example, ethanol, preferably at reflux.

Intermediates of formula (IX) wherein X is —CH$_2$CH$_2$— may be prepared by the reaction of a compound of the formula Ar$^1$—CHO with a compound of formula (X)

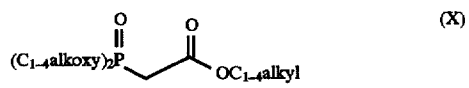

in the presence of a base, for example, an alkali metal hydride such as sodium hydride and in a suitable solvent, for example, an ether such as tetrahydrofuran. In the compound of formula (X), C$_{1-4}$alkoxy is preferably ethoxy and C$_{1-4}$alkyl is preferably ethyl.

Compounds of the formula Ar$^1$—CHO and formula (X) are commercially available compounds, or may be prepared by known procedures.

Intermediates of formula (III) are either commercially available compounds or may be prepared in a conventional manner, for example, by the reaction of a compound of the formula Ar$^2$—Y—NH$_2$ with 4-nitrophenyl chloroformate in the presence of an acylation catalyst such as DMAP, followed by reaction with a strong alkali, for example, sodium hydroxide.

Compounds of formulae (IV), (Va) to (Ve), (VI) and (VII) are commercially available, or may be prepared from commercially available starting materials using conventional procedures well known to those skilled in the art.

Where the above-described processes for the preparation of the compounds according to the invention give rise to mixtures of stereoisomers these isomers may, if desired, be separated, suitably by conventional techniques such as preparative chromatography.

The novel compounds may be prepared in racemic form, or individual enantiomers may be prepared either by enantiospecific synthesis or by resolution. For example, compounds which contain a hydroxy group may be resolved into their component enantiomers by standard techniques, such as the formation of diastereomeric esters or amides, followed by chromatographic separation or separation by fractional crystallization and removal of the chiral auxiliary. Where these are intermediates, diastereoisomers can then be used to prepare optically pure compounds of formula (I).

During any of the above synthetic sequences it may be necessary and/or desirable to protect sensitive or reactive groups on any of the molecules concerned. This may be achieved by means of conventional protecting groups, such as those described in *Protective Groups in Organic*

*Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The exemplified compounds of this invention were tested by the methods set out at pages 36 to 39 of International Patent Specification No. WO 93/01165. The compounds were found to be active with $IC_{50}$ at the NK1 receptor of less than 150 nM.

The compounds of this invention may be formulated as specifically illustrated at pages 35 to 36 of International Patent Specification No. WO 93/01165.

The following non-limiting examples serve to illustrate the present invention:

DESCRIPTION 1

3,5-Bis(trifluoromethyl)phenethyl Hydrazide

To the anion of methyl diethylphosphonoacetate (generated from methyl diethylphosphonoacetate (12.21 ml, 0.061 mol) and sodium hydride (0.067 mol) (in 50 ml THF) was added 3,5-bis(trifluoromethyl)benzaldehyde, dropwise, at 0° C. The reaction was stirred for 2 hours and diluted with ethyl acetate (300 ml) and water (200 ml). The ethyl acetate layer was dried ($MgSO_4$) and solvent removed in vacuo. The oil obtained was dissolved in ethanol (50 ml) and hydrogenated at 50 psi using palladium on carbon (1 g) for 3 hours. The catalyst was filtered and the ethanol solution treated with hydrazine hydrate (13 ml, 0.41 mol) and heated to reflux at 100° C. for 16 hours. The ethanol was removed and the residue partitioned between ethyl acetate (200 ml) and water (50 ml). The organic layer was washed with brine and dried ($MgSO_4$). Removal of the solvent in vacuo gave a white crystalline solid which was recrystallized from ethyl acetate/60°–80° petroleum ether to give the title compound. (10 g, 81%).

$^1$H NMR ($CDCl_3$) δ 7.72 (1H,s), 7.66 (2H,s), 6.70 (1H,s), 3.90 (2H,brs), 3.16 (2H,t), 2.5 (2H,t).

DESCRIPTION 2

3-(3,5-Bis(trifluoromethyl)phenethyl)-4-benzyl-1-(3-chloropropyl)-5-oxo-1,2,4-triazole 3-(3,5-Bis(trifluoromethyl)phenethyl)-4-benzyl-1H-5-oxo-1,2,4-triazole (Example 1) (3 g, 0.0072 mol) was dissolved in anhydrous DMF (20 ml) and sodium hydride (0.390 g) added. The reaction was stirred for 0.5 hours at 25° C. and 3-iodo-1-chloropropane (0.78 ml) added. The reaction was stirred for a further 2 hours and quenched with water (20 ml). The product was extracted into ethyl acetate (50 ml), the organic layer washed with water (20 ml×3), brine and dried ($MgSO_4$). Filtration, removal of solvent in vacuo and chromatography of the resulting oil on silica eluting with 20% ethyl acetate/hexane furnished the title compound as a colourless oil. (2.7 g, 76%).

$^1$H NMR ($CDCl_3$) δ 7.72 (1H,s), 7.52 (2H,s), 7.18–7.0 (5H,m), 4.82 (2H,s), 3.98 (2H,t), 3.56 (2H,t), 2.98 (1H,t), 2.7 (2H,t), 2.2 (2H,m).

DESCRIPTION 3

(+) 3-(3,5-Bis(trifluoromethyl)phenethyl)-4-benzyl-1-(3-chloro-2-methyl)propyl-5-oxo-1,2,4-triazole Prepared as for the compound of Description 2 using the compound of Example 1 and 3-iodo-2-methyl-chloropropane. $^1$H NMR ($CDCl_3$) δ 7.64 (1H,s), 7.42 (2H,s), 7.26 (3H,m), 7.12 (2H,m), 4.74 (2H,s), 3.72 (2H,m), 3.44 (2H,m), 2.83 (2H,t), 2.62 (2H,t), 2.34 (1H,m).

EXAMPLE 1

3-(3,5-Bis(trifluoromethyl)phenethyl)-4-benzyl-1H-5-oxo-1,2,4-triazole

To a solution of 3,5-bis(trifluoromethyl)phenethyl hydrazide (1.8 g) in methanol (10 ml) and dichloromethane (30 ml) was added benzylisocyanate (0.92 ml). The solution was stirred for 2 hours and the resulting white precipitate filtered and washed with hexane. The precipitate was redissolved in methanol (15 ml) and sodium hydroxide (4N, 15 ml) and heated to reflux for 2 hours. The methanol was removed in vacuo and the product extracted into ethyl acetate (50 ml). The organic layer was washed with brine, dried ($MgSO_4$), and the solvent removed in vacuo to give a white solid. Recrystallization from ethyl acetate/petroleum ether gave the title compound (2.0 g, 80%).

$^1$H NMR ($CDCl_3$) δ 9.90 (1H,s), 7.72 (1H,s), 7.50 (2H,s), 7.16–7.42 (5H,m), 4.88 (2H,s), 3.0 (2H,t), 2.7 (2H,t).

EXAMPLE 2

3-(3,5-Bis(trifluoromethyl)phenethyl)-4-benzyl-1-(3-aminopropyl)-5-oxo-1,2,4-triazole 3-(3,5-Bis(trifluoromethyl)phenethyl)-4-benzyl-1-(3-chloropropyl)-5-oxo-1,2,4-triazole (Description 2, 2.5 g, 0.005 mol) was dissolved in DMF (30 ml) and sodium azide (0.495 g, 0.0076 mol) added and the reaction heated to 80° C. for 16 hours. The reaction was cooled, diluted with water (50 ml) and extracted into ethyl acetate (75 ml). The organic layer was washed with water (3×25 ml), brine and dried ($MgSO_4$). The solvent was removed and the resulting azide (colourless oil) was dissolved in ethanol (30 ml) and hydrogenated over palladium hydroxide (0.300 g) at 50 psi for 4 hours. The catalyst was filtered and the solvent removed in vacuo to furnish the title compound as a colourless oil. (2.4 g).

$^1$H NMR ($CDCl_3$) δ 7.64 (1H,s), 7.44 (2H,s), 7.3 (3H,m), 7.14 (2H,s), 4.74 (2H,s), 3.66 (2H,t), 3.3 (2H,t), 2.90 (2H,t), 2.62 (2H,t), 1.96 (2H,m).

EXAMPLE 3

3-(3,5-Bis(trifluoromethyl)phenethyl)-4-benzyl-1-(2-aminobenzyl)-5-oxo-1,2,4-triazole 3-(3,5-Bis(trifluoromethyl)phenethyl)-4-benzyl-1H-5-oxo-1,2,4-triazole (Example 1, 1.0 g, 0.0024 mol) was dissolved in anhydrous DMF (10 ml) and sodium hydride (0.130 g, 0.0031 mol) added. After stirring for 0.5 hours at 25° C., o-nitrobenzylbromide was added and the reaction stirred for a further 2 hours. The reaction was then diluted with ethyl acetate (50 ml) and washed with water (20 ml×3), brine and dried ($MgSO_4$). The solvent was removed in vacuo and the residue chromatographed on silica eluting with 30–40% ethyl acetate/hexane to obtain 3-(3,5-bis(trifluoromethyl)phenethyl)-4-benzyl-1-(2-nitrobenzyl)-5-oxo-1,2,4-triazole (1.0 g, 76%) as a colourless oil. The oil was dissolved in ethanol (30 ml) and tin(II)chloride dihydrate (2.05 g, 0.009 mol, 5 eq.) was added. The reaction was stirred at 25° C. for 16 hours and the solvent evaporated in vacuo. The residue was partitioned between ethyl acetate/water (50 ml/20 ml). The organic layer was washed with saturated sodium bicarbonate solution, brine, and dried (MgSO$_4$). The solvent was removed to give a white solid and recrystallization from ether/petrol yielded the title compound. (0.800 g, 85%).

$^1$H NMR (d$_6$-DMSO) δ 8.02 (3H,s), 7.30–7.54 (5H,m), 7.12 (1H,dt), 6.98 (1H,dt), 6.78 (1H,dd), 6.62 (1H,dt), 5.32 (2H,s), 5.06 (2H,s), 4.86 (2H,s), 3.12 (2H,t), 3.0 (2H,t).

EXAMPLE 4

3-(3,5-Bis(trifluoromethyl)phenethyl)-4-benzyl-4-(3-aminobenzyl)-5-oxo-1,2,4-triazole Prepared as for the compound of Example 3 using m-nitrobenzyl bromide. The title compound was obtained as a white solid.

$^1$H NMR (250 MHz, CDCl$_3$) δ 2.64 (2H,t), 2.88 (2H,t), 4.79 (2H,s), 5.02 (2H,s), 7.12–7.51 (8H,m), 7.57–7.66 (2H, m), 8.08–8.15 (2H,m).

EXAMPLE 5

3-(3,5-Bis(trifluoromethyl)phenethyl)-4-benzyl-1-(4-aminobenzyl)-5-oxo-1,2,4-triazole Prepared as for the compound of Example 3 using p-nitrobenzyl bromide.

MS (ES)$^+$ Da/e 521 ((M+1)$^+$, 100%).

EXAMPLE 6

3-(3,5-Bis(trifluoromethyl)phenethyl)-4-benzyl-1-(3-(4phenylpiperidino)propyl)-5-oxo -1,2,4-triazole 3-(3,5-Bis(trifluoromethyl)phenethyl)-4-benzyl-1-(3-chloro)propyl-5-oxo-1,2,4-triazole (Description 2, 0.500 g, 0.0012 mol), DMF (10 ml), potassium carbonate (0.333 g, 0.0024 mol) and 4-phenylpiperidine (0.290 g, 0.0018 mol) were heated at 100° C. for 16 hours. The reaction was cooled and partitioned between ethyl acetate (100 ml) and water (30 ml). The organic layer was collected and washed with water (3×20 ml), dried (MgSO$_4$), evaporated and the residue chromatographed on silica eluting with dichloromethane, followed by 1% methanol/dichloromethane rising to 3% then 5%. The oil thus obtained was treated with hydrochloric acid/methanol, the methanol removed in vacuo and freeze-dried from acetonitrile/water to give the title compound as a white solid (850 g, 57%).

$^1$H NMR (CDCl$_3$) δ 7.74 (1H,s), 7.54 (2H,s), 7.18–7.40 (10H,m), 4.80 (2H,s), 3.94 (2H,m), 3.68 (2H,m), 3.10 (2H, m), 3.0 (2H,m), 2.66 (5H,m), 2.48 (2H,m), 2.0 (5H,m). MS (m/e) 617 (100%, M+1)

EXAMPLE 7

3-(3,5-Bis(trifluoromethyl)phenethyl)-4-benzyl-1-(3-(3-indoleacetamido)propyl)-5-oxo-1,2,4-triazole 3-(3,5-Bis(trifluoromethyl)phenethyl)-4-benzyl-1-(3-aminopropyl)-5-oxo-1,2,4-triazole (Example 2, 0.500 g, 0.0010 mol) was dissolved in dichloromethane (20 ml) and indole-3-acetic acid (0.222 g, 0.00127 mol), 1-(3-dimethylamino-propyl)-3-ethylcarbodiimide.HCl (0.244 g, 0.00127 mol), hydroxybenzotriazole (0.171 g, 0.00127 mol) and triethylamine (0.7 ml, 0.005 mol) added. The reaction was stirred for 16 hours, diluted with ethyl acetate (50 ml), washed with 10% citric acid solution, saturated sodium bicarbonate solution and brine. The organic layer was dried (MgSO$_4$) and solvent evaporated. The residue was chromatographed on silica eluting with ethyl acetate then 1% methanol/ethyl acetate, to give the title compound as a pale yellow solid (0.500 g 80%).

$^1$H NMR (CDCl$_3$) δ 8.32 (1H,brs), 7.64 (1H,s), 7.54 (1H,d), 7.38 (2H,s), 7.24 (4H,m), 7.06 (5H,m), 6.32 (1H,t), 4.64 (2H,s), 3.84 (4H,m), 3.10 (2H,m), 2.80 (2H,t), 2.52 (2H,t), 1.76 (2H,m). MS (m/z): 630 (M+1, 50%), 647 (M$^+$+NH$_4^+$, 10%)

EXAMPLE 8

3-(3,5-Bis(trifluoromethyl)phenethyl)-4-benzyl-1-(3-(4,4'-indenylpiperidino)propyl)-5-oxo-1,2,4-triazole Prepared as for Example 6 using 3-(3,5-bis (trifluoromethyl)phenethyl)-4-benzyl-1-(3-chloropropyl)-5-oxo-1,2,4-triazole (Description 2) and 4,4'-indenylpiperidine. The compound was isolated as the HCl salt after freeze-drying to a white solid from acetonitrile/water.

$^1$H NMR (CDCl$_3$) δ 7.34 (1H,s), 7.14 (2H,s), 6.80–7.0 (9H,m), 6.48 (1H,d), 6.38 (1H,d), 4.50 (2H,s), 3.54 (2H,t), 2.64 (4H,m), 2.30 (2H,t), 2.10 (2H,t), 1.96–1.20 (4H,m) 1.66 (2H,m), 1.20 (2H,brd). MS m/e (Cl$^+$) 641 (100%, M+1).

EXAMPLE 9

3-(3,5-Bis(trifluoromethyl)phenethyl)-4-benzyl-1-(3-(4-benzylpiperidino)propyl)-5-oxo-1,2,4-triazole Prepared as for Example 6 using 3-(3,5-bis(trifluoromethyl)phenethyl)-4-benzyl-1-(3-chloropropyl)-5-oxo-1,2,4-triazole (Description 2) and 4-benzylpiperidine. MS m/e (Cl$_+$) 631 (100%, M+1).

EXAMPLE 10

3-(3,5-Bis(trifluoromethyl)phenethyl)-4-benzyl-1-(3-(4,4'-(N-sulfonamidomethylindolinyl)piperidino) propyl)-5-oxo-1,2,4-triazole Prepared as for Example 6 using 3-(3,5-bis (trifluoromethyl)phenethyl)-4-benzyl-1-(3-chloropropyl)-5-oxo-1,2,4-triazole (Description 2) and 4,4'-(N-sulfonamidomethylindolinyl)piperidine. The title compound was isolated as the HCl salt. MS (Cl$^+$) m/z 722 (M+1)$^+$, 78%.

EXAMPLE 11

3-(3,5-Bis(trifluoromethyl)phenethyl)-4-benzyl-1-(3-(1,2,3,4-tetrahydroisoquinolin-2-yl)propyl)-5-oxo-1, 2,4-triazole Prepared as for Example 6 using 3-(3,5-bis (trifluoromethyl)phenethyl)-4-benzyl-1-(3-chloropropyl)-5-oxo-1,2,4-triazole (Description 2) and tetrahydroisoquinoline. The title compound was isolated as the HCl salt.

$^1$H NMR (360 MHz, d$_6$-DMSO) δ 7.92 (1H,s), 7.90 (2H,s), 7.36–7.19 (9H,m), 4.88 (2H,s), 4.53–4.30 (1H,m), 4.29–4.25 (1H,m), 3.82 (2H,t,5–6.8 Hz) 3.27–3.24 (4H,m), 3.03–3.01 (3H,m), 2.86 (2H,t,J=8.2 Hz), 2.22–2.20 (ZH,m). MS (m/e) (Cl$^+$) 589 (M+1)$^+$.

EXAMPLE 12

3-(3,5-Bis(trifluoromethyl)phenethyl)-4-benzyl-1-(3-(3,4-dichlorobenzamido)benzyl)-5-oxo-1,2,4-triazole The compound of Example 4 (0.250 g, 0.48 mmol) was dissolved in dichloromethane (10 ml) and triethylamine (0.1 ml, 0.72 mmol) was added followed by 3,4-dichlorobenzoyl chloride (0.120 g, 0.58 mmol) and N,N-dimethylaminopyridine (0.5 mg). The reaction was stirred at 25° C. for 16 hours, diluted with ethyl acetate (30 ml) and washed with water (10 ml) and brine. The organic layer was dried (MgSO$_4$), solvent removed in vacuo and the residue chromatographed on silica eluting with 30% ethyl acetate/hexane to furnish the title compound as a white solid. (0.300 g, 90%).

$^1$H NMR (CDCl$_3$) δ 7.96 (2H,m), 7.70 (3H,m), 7.57 (1H,s), 7.53 (1H,s), 7.47 (2H,s), 7.24–7.38 (3H,m), 7.10–7.22 (3H,m), 4.98 (2H,s), 4.8 (2H,s), 2.96 (2H,t), 2.66 (2H,t). MS (CI$^+$) m/z 693 (M+1)$^+$.

EXAMPLE 13

3-(3,5-Bis(trifluoromethyl)phenethyl)-4-benzyl-1-(2-(benzenesulfonamido)benzyl)-5-oxo-1,2,4-triazole Prepared by the method analogous to that described for Example 12 using the compound of Example 3 and benzenesulfonyl chloride. The title compound was isolated as a white solid (70%).

$^1$H NMR (DMSO) δ 7.92 (1H,s), 7.88 (2H,s), 7.50–7.74 (5H,m), 7.06–7.40 (5H,m), 6.84 (2H, dd), 4.90 (2H,s), 4.84 (2H,s), 3.0 (2H,t), 2.90 (2H,t). MS (m/z) 678 (10%, M+NH$_4$$^+$), 521 (45%, (M—PhSO$_2$)+2).

EXAMPLE 14

3-(3,5-Bis(trifluoromethyl)phenethyl)-4-benzyl-1-(3-(3,4-dichloro-(N-methyl)benzamido)benzyl)-5-oxo-1,2,4-triazole The compound of Example 12 (0.187 g, 0.27 mmol) was dissolved in DMF (10 ml) and sodium hydride (0.016 g, 0.40 mmol) was added followed by iodomethane (0.025 ml, 0.40 mmol). The solution was stirred at 25° C. for 16 hours and diluted with ethyl acetate (30 ml) and water (20 ml). The organic layer was collected and washed with water (3×50 ml), dried (MgSO$_4$) and filtered and the solvent evaporated. The residue was chromatographed on silica eluting with 30% ethyl acetate/hexanes to yield the title compound as a colourless oil. (84%).

$^1$H NMR (CDCl$_3$) δ 7.74 (1H,s), 7.48 (2H,s), 7.46 (1H, d,J=2 Hz), 7.34 (3H,m), 7.24 (5H,m), 6.96–7.08 (3H,m), 4.9 (2H,s), 4.84 (2H,s), 3.46 (3H,t), 2.92 (2H,t), 2.66 (2H,t).

EXAMPLE 15

3-(3,5-Bis(trifluoromethyl)phenethyl)-4-benzyl-1-(3-(4,4'-(3,3'-indanyl)piperidinopropyl)-5-oxo-1,2,4-triazole Prepared as for Example 6 using 3,5-bis(trifluoromethyl)phenethyl)-4-benzyl-1-(3-chloropropyl)-5-oxo-1,2,4-triazole (Description 2) and 4,4'-(3,3'-indanyl)piperidine. The title compound was isolated as the HCl salt.

$^1$H NMR (d$_6$-DMSO) δ 7.94 (1H,s), 7.92 (2H,s), 7.10–7.20 (9H,m), 4.90 (2H,s), 3.80 (2H,t), 3.48 (2H,brd), 3.10–3.20 (6H,m), 2.88 (4H,q), 2.0–2.3 (6H,m), 1.64 (2H, brd). MS m/z (CI$^+$): 643 (M+1)$^+$.

EXAMPLE 16

3-(3,5-Bis(trifluoromethyl)phenethyl)-4-benzyl-1-(3-(3-hydroxyprridyl)propyl)-5-oxo-1,2,4-triazole 3-Hydroxypyridine (0.500 g, 0.0053 mol) was dissolved in DMF (10 ml) and sodium hydride (0.212 g) added. The reaction was stirred for 20 minutes and 3-(3,5-bis(trifluoromethyl)phenethyl)-4-benzyl-1-(3-chloropropyl)-5-oxo-1,2,4-triazole (Description 2, 0.500 g, 0.0010 mol) added and the reaction stirred at 80° C. for 16 hours. The reaction was cooled, water (30 ml) added and the product extracted into ethyl acetate (50 ml). The ethyl acetate layer was washed with water (3×20 ml), dried (MgSO$_4$) and solvent removed in vacuo. The residue was chromatographed on silica eluting with ethyl acetate to furnish the title compound as a white solid (0.480 g, 87%).

$^1$H NMR (DMSO) δ 8.24 (1H,m), 8.16 (1H,m), 7.64 (1H,s), 7.44 (2H,s), 7.24 (3H,m), 7.10 (4H,m), 4.74 (2H,s), 4.0 (4H,m), 2.84 (2H,t), 2.60 (2H,t), 2.20 (2H,m). MS m/z 551 (M+1).

EXAMPLE 17

3-(3,5-Bis(trifluoromethyl)phenethyl)-4-benzyl-1-(3-(N-methylpiperazino)propyl)-5-oxo-1,2,4-triazole Prepared as for Example 6 using the title compound of Description 2 and N-methyl piperazine. The title compound was isolated as the HCl salt.

$^1$H NMR (DMSO) δ 7.92 (3H,s), 7.19–7.40 (5H,m), 4.90 (2H,s), 3.1–3.84 (11H,m), 3.04 (2H,t), 2.84 (5H,m), 2.54 (3H,s), 2.06 (2H,m). MS m/e (CI$^+$) 556 (M+1)+.

EXAMPLE 18

3-(3,5-Bis(trifluoromethyl)phenethyl)-4-benzyl-1-[3-(4-phenylpiperidino)-2-methylpropyl]-5-oxo-1,2,4-triazole Prepared in an analogous manner to Example 6 using the compound of Description 3 and 4-phenylpiperidine. The title compound was converted to the HCl salt and freeze-dried to a white solid.

$^1$H NMR (360 MHz, d$_6$-DMSO) δ 7.91 (1H,s), 7.88 (2H,s), 7.37–7.22 (10H,m), 4.90 (2H,s), 3.87–3.82 (1H,m), 3.72–3.66 (1H,m), 3.04–2.77 (9H,m), 2.43–2.41 (1H,m), 2.24–2.17 (2H,m), 1.95–1.91 (2H,m), 0.95–0.91 (2H,m).

EXAMPLE 19

3-(3,5-Bis(trifluoromethyl)phenethyl)-4-benzyl-1-(3-(3,4-dichlorobenzylamino)benzyl)-5-oxo-1,2,4-triazole 3,4-Dichlorobenzaldehyde (0.10 g) and magnesium sulphate (0.69 g) were added to a solution of the compound of Description 5 (0.30 g) in dichloromethane (2 ml) and the mixture was stirred at room temperature for 18 hours. The magnesium sulphate was filtered off and the filtrate was concentrated in vacuo. The residue was dissolved in ethanol (5 ml) and cooled to 0° C. before addition of sodium borohydride (0.022 g). The mixture was allowed to warm to room temperature and stirred for 2 hours. Ethanol was removed in vacuo, water was added to the residue and the product extracted into ethyl acetate (×2). The combined organics were dried (MgSO$_4$) and concentrated. The material was purified by gradient chromatography on silica using 20% to 40% ethyl acetate in petroleum ether 60–80 as eluent, to give the title compound. MS (CI$^+$) m/z 679 ((M+1)$^+$60%).

The following compounds were prepared as for Example 6 using the compound of Description 2 and the corresponding amine.

EXAMPLE 20

3-(3,5-Bis(trifluoromethyl)phenethyl)-4-benzyl-1-(3-(1,2,3,4-tetrahydroquinolin-1-yl)propyl)-5-oxo-1,2,4-triazole $^1$H NMR (360 MHz, d$_6$-DMSO) δ 7.87 (3H,m), 7.35–7.20 (5H,m), 6.95–6.89 (2H,m), 6.56 (2H,s), 4.87 (2H,s), 3.73

(2H,t,J=6.74 Hz), 3.25–3.17 (4H,m), 3.03 (2H,t,J=7.4 Hz), 2.87 (2H,t,J=7.3 Hz), 2.67 (2H,t,J=6.3 Hz), 1.89–1.83 (4H, m). MS (CI$^+$) m/e 589 (M+1)$^+$.

EXAMPLE 21

3-(3,5-Bis(trifluoromethyl)phenethyl)-4-benzyl-1-(3-(piperidin-1-yl)propyl)-5-oxo-1,2,4-triazole MS (CI$^+$) m/e 541 (M+1)$^+$.

EXAMPLE 22

3-(3,5-Bis(trifluoromethyl)phenethyl)-4-benzyl-1-(3-(1,2,4-triazol-1-yl)propyl)-5-oxo-1,2,4-triazole $^1$H NMR (350 MHz, d$_6$-DMSO) δ 7.88 (3H,s), 7.60 (1H,s), 7.36–7.13 (5H,m), 6.88 (1H,s), 4.86 (2H,s), 3.93 (2H,t,J=6.7 Hz), 3.63 (2H,t,J=6.7 Hz), 3.03 (2H,t,J=7.4 Hz), 2.86 (2H,t,J=7.4 Hz), 2.06–1.99 (2H,m). MS (CI$^+$) m/e 524 (M+1)$^+$.

EXAMPLE 23

3-(3,5-Bis(trifluoromethyl)phenethyl)-4-benzyl-1H-5-mercapto-1,2,4-triazole

A suspension of the compound of 3,5-bis(trifluoromethyl) phenethyl hydrazide (Description 1) (1.0 g) and benzyl isothiocyanate (0.53 ml) in 1-butanol (20 ml) was heated to reflux for 10 minutes. The mixture was allowed to cool slightly and 1,8-diazabicyclo[5.4.0]undec-7-ene (0.3 ml) added. The reaction mixture was then heated to reflux for 2 hours. Solvent was removed in vacuo and the residue was partitioned between water and dichloromethane. The organic layer was dried (MgSO$_4$) and concentrated. The residue was purified by gradient chromatography on silica eluting with 10%–60% ethyl acetate in petroleum ether. The product was recrystallised from ethyl acetate/petrol to give the title compound.

MS (CI$^+$) m/z 432 ((M+1)$^+$ 100%).

EXAMPLE 24

3-(3,5-Bis(trifluoromethyl)phenethyl)-4-benzyl-1-(3-(3-indoleacetamido)benzyl)-5-oxo-1,2,4-triazole Prepared as for Example 7 using compound of Example 4 and 3-indoleacetic acid.

MS (CI$^+$) m/z 678 (M+1)$^+$ 5%

696 (M+18)$^+$ 15%

Elemental analysis: Calc. C,63.81; H,4.31, N, 10.34; Found C,63.56; H,4.27; N,10.14%

EXAMPLE 25

3-(3,5-Bis(trifluoromethyl)phenethyl)-4-benzyl-1-(4-(3,4-dichlorophenylacetamido)benzyl)-5-oxo-1,2,4-triazole Prepared as for Example 7 using the compound of Example 5 and 3,4-dichlorophenylacetic acid.

MS (CI$^+$) m/z 724 [(M+18)$^+$, 8%].

EXAMPLE 26

3-(3,5-Bis(trifluoromethyl)phenethyl)-4-benzyl-1-(4-(3,4-dichlorophenylamido)benzyl)-5-oxo-1,2,4-triazole Prepared as for Example 12 using the compound of Example 5 and 3,4-dichlorobenzoyl chloride.

MS (CI$^+$) m/z 710 ((M+18)$^+$ 5%).

EXAMPLE 27

3-(3,5-Bis(trifluoromethyl)phenethyl)-4-benzyl-1-(2-(4-phenylpiperidino)ethyl)-5-oxo-1,2,4-triazole Step 1: 3-(3,5-Bis(trifluoromethyl)phenethyl)-4-benzyl-1-allyl-5-oxo-1,2,4-triazole (a)

Prepared as for compound of Description 2 using 3-(3,5-bis(trifluoromethyl)phenethyl)-4-benzyl-1H-5-oxo-1,2,4-triazole (Example 1) and allyl bromide.

$^1$H NMR (360 MHz, CDCl$_3$) δ 7.71 (1H,s), 7.50 (2H,s), 7.34–7.19 (5H,m), 5.97–5.86 (1H,m), 5.26 (1H,s), 5.22 (1H,d,J=7.6 Hz), 4.82 (2H,s), 4.41 (1H,d,J=7.6 Hz), 2.95 (2H,t,J=7.6 Hz), 2.68 (2H,t,J=7.6 Hz).

Step 2: 3-(3,5-Bis(trifluoromethyl)phenethyl)-4-benzyl-1-acetaldehydo-5-oxo-1,2,4-triazole (b)

The above compound (a) (1.6 g) was dissolved in methanol/dichloromethane (1:1) and cooled to −78° C. Ozone was bubbled through the reaction mixture until TLC indicated complete reaction. Dimethyl sulphide (2 ml) was added and the reaction was stirred for 6 hours. The solvent was removed and the residue was purified by chromatography on silica using ethyl acetate to yield the title compound (1.4 g).

$^1$H NMR (360 MHz, CDCl$_3$) δ 9.68 (1H,s), 7.72 (1H,s), 7.50 (2H,s), 7.36–7.21 (5H,m), 2.97 (2H,t,J=7.6 Hz), 2.70 (2H,t,J=7.6 Hz). MS (CI$^+$) 458 (M+H$^+$).

Step 3: 3-(3,5-Bis(trifluoromethyl)phenethyl)-4-benzyl-1H-5-mercapto-1,2,4-triazole Aldehyde (b) above (457 mg) and 4-phenylpiperidine (161 mg) were added to a solution of acetic acid (0.2 ml) in methanol (10 ml). Sodium cyanoborohydride was added and the reaction was stirred for 16 hours. The solvent was removed and the residue was partitioned between ethyl acetate and water. The organic layer was dried (MgSO$_4$), filtered and evaporated to yield an oil. Purification by chromatography on silica using dichloromethane/methanol (95:5), yielded an oil, which was treated with HCl to give the title compound as the hydrochloride salt.

$^1$H NMR (360 MHz, d$_6$-DMSO) δ 10.49 (1H,brs), 7.92 (1H,s), 7.90 (2H,s), 7.36–7.24 (10H,m), 4.88–4.90 (1H,m), 4.16–4.19 (1H,m), 3.63–3.64 (1H,m), 3.38–3.41 (1H,m), 3.06–2.80 7H,m), 1.80–2.10 (4H,m). MS (CI$^+$) 603 (M+H$^+$).

EXAMPLE 28

3-(3,5-Bis(trifluoromethyl)phenethyl)-4-benzyl-1-(3-(4-phenylpiperidino)-2-methylenopropyl)-5-oxo-1,2,4-triazole The compound from Example 1 (830 mg) in dry DMF (10 ml) was treated with sodium hydride (60%) (120 mg) and 3-chloro-2-chloromethylprop-1-ene. The reaction was stirred for 16 hours, poured into water and extracted with ethyl acetate. The organic layer was washed with brine/water (1:1) (×4), dried (MgSO$_4$) filtered and evaporated. The residue was heated in DMF (10 ml) and 4-phenylpiperidine at 80° C. for 4 hours. After work-up the oil obtained was purified by chromatography on silica using dichloromethane/methanol (97:3) to give an oil which was treated with hydrogen chloride to give the HCl salt of the title compound as a solid.

$^1$H NMR (360 MHz, d$_6$-DMSO) δ 10.80–10.92 (1H,brs), 7.89 (1H,s), 7.86 (2H,s), 7.36–7.22 (10H,m), 5.50 (1H,s), 4.94–4.93 (3H,m), 4.57 (2H,s), 3.76 (2H,d,J=5.2 Hz), 3.49 (2H,d,J=11.5 Hz), 3.06–2.78 (7H,m), 2.53–2.46 (2H,m), 1.96 (2H,d,J=12.7 Hz).

EXAMPLE 29

3-(3,5-Bis(trifluoromethyl)phenethyl)-4-benzyl-1-(3,4-dichlorobenzyl)-5-oxo-1,2,4-triazole Prepared as for the compound of Description 2 using 3-(3,5-bis(trifluoromethyl)phenethyl)-4-benzyl-1H-5-oxo-1,2,4-triazole (Example 1) and 3,4-dichlorobenzyl chloride.

$^1$H NMR (250 MHz, CDCl$_3$) δ 7.72 (1H,s), 7.48 (2H,s), 7.42 (1H,d,J=2 Hz), 7.32 (3H,m), 7.20 (4H,m), 4.92 (2H,s), 4.84 (2H,s), 2.92 (2H,t,J=7 Hz). MS (CI⁻) m/e 573 (M–1)⁺.

EXAMPLE 30

3-(3,5-Bis(trifluoromethyl)phenethyl)-4-benzyl-1-(2-phenylethyl)-5-oxo-1,2,4-triazole Prepared as for compound of Description 2 using 3-(3,5-bis(trifluoromethyl)phenethyl)-4-benzyl-1H-5-oxo-1,2,4-triazole (Example 1) and phenethyl bromide.

$^1$H NMR (250 MHz, CDCl$_3$) δ 7.72 (1H,s), 7.5 (2H,s), 7.14–7.34 (8H,m), 7.1 (2H,m), 4.8 (2H,s) 4.06 (2H,t), 3.08 (2H,t), 2.92 (2H,t), 2.66 (2H,t).

We claim:

1. A compound of the formula (I) or a pharmaceutically acceptable salt thereof:

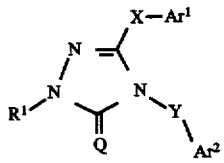

(I)

wherein Ar$^1$ represents phenyl optionally substituted by 1, 2 or 3 groups selected from C$_{1-6}$alkyl, C$_{2-6}$alkenyl, C$_{2-6}$alkynyl, C$_{3-7}$cycloalkyl, C$_{3-7}$cycloalkylC$_{1-4}$alkyl, halo, cyano, nitro, trifluoromethyl, trimethylsilyl, —OR$^a$, —SR$^a$, —SOR$^a$, —SO$_2$R$^a$, —NR$^a$R$^b$, —NR$^a$COR$^b$, —NR$^a$CO$_2$R$^b$, —COR$^a$, —CO$_2$R$^a$ or —CONR$^a$R$^b$, where and R$^a$ and R$^b$ each independently represent H, C$_{1-6}$alkyl, phenyl or trifluoromethyl;

Ar$^2$ represents aryl selected from phenyl and naphthyl; heteroaryl selected from indolyl, indazolyl, thienyl, furyl, pyridyl, thiazolyl, triazolyl, tetrazolyl and quinolyl; benzhydryl; or benzyl; wherein each aryl and heteroaryl and each phenyl moiety of benzyl and benzhydryl may be substituted by 1, 2 or 3 groups selected from C$_{1-6}$alkyl, C$_{1-6}$alkoxy, CO$_2$C$_{1-4}$alkyl, cyano, halo and trifluoromethyl;

R$^1$ represents a group of the formula Z-R$^2$;

R$^2$ represents a group of the formula (iv):

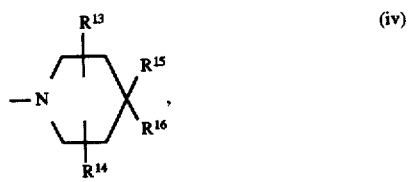

(iv)

R$^3$, R$^4$, R$^5$ and R$^6$ each independently represent H or C$_{1-4}$alkyl;

R$^7$ and R$^8$ each independently represent H, C$_{1-6}$alkyl, trifluoromethyl, phenyl or benzyl;

R$^{13}$ and R$^{14}$ each independently represent H or C$_{1-6}$alkyl;

R$^{15}$ and R$^{16}$ together form an indane or indene ring or an indoline ring which is substituted on the nitrogen atom by R$^{18}$, any of which rings can be substituted on the phenyl moiety by 1 or 2 groups selected from halo, C$_{1-6}$alkyl, C$_{1-6}$alkenyl, C$_{1-6}$alkoxy, CO$_2$C$_{1-4}$alkyl, trifluoromethyl and cyano;

R$^{18}$ represents H, CO$_2$R$^{19}$, CONR$^7$R$^8$, SONR$^7$R$^8$ or SO$_2$R$^{19}$;

R$^{19}$ represents C$_{1-6}$alkyl, phenyl or benzyl;

Q represents O or S;

X represents a group selected from —CR$^3$R$^4$CR$^5$R$^6$-, —CR$^3$=CR$^4$—, —C(OH)R$^3$CR$^4$R$^5$-, —CR$^3$R$^4$C(OH)R$^5$-, —C(O)CR$^3$R$^4$- and —CR$^3$R$^4$C(O)—;

Y represents a C$_{1-4}$alkylene chain; and

Z represents a straight or branched C$_{1-6}$alkylene or C$_{3-6}$alkenylene chain with the proviso that the alkenylene double bond does not terminate at a carbon atom attached to a nitrogen atom.

2. A compound as claimed in claim 1 of the formula (Ia) or a pharmaceutically acceptable salt thereof:

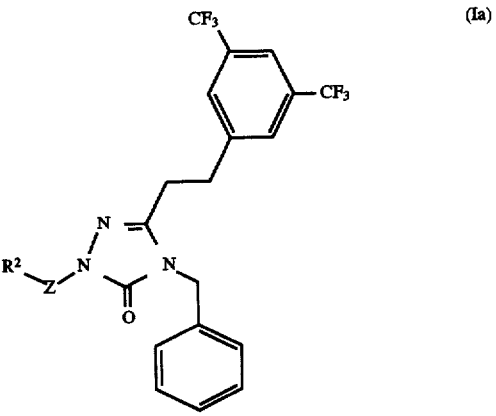

(Ia)

wherein R$^2$ and Z are as defined in claim 1.

3. A compound as claimed in claim 1 wherein Ar$^1$ represents phenyl substituted by 1, 2 or 3 substituents selected from nitro, trifluoromethyl, trimethylsilyl, bromo, chloro, fluoro, iodo, cyano, methyl, ethyl, cyclopropyl, t-butyl, vinyl, methoxy, phenoxy, amino and carbonylmethoxy.

4. A compound as claimed in claim 1 wherein Ar$^2$ represents unsubstituted or substituted phenyl.

5. A compound as claimed in claim 1 wherein Q is O.

6. A compound as claimed in claim 1 wherein X represents —CR$^3$R$^4$CR$^5$R$^6$-.

7. A compound as claimed in claim 6 wherein R$^3$, R$^4$, R$^5$ and R$^6$ each independently represent H.

8. A compound as claimed in claim 1 wherein Z represents a C$_{1-4}$alkylene chain.

9. A compound as claimed in claim 1 wherein R$^2$ represents a group of formula (iv) where R$^{13}$ and R$^{14}$ are both H and R$^{15}$ and R$^{16}$ together form an indane or indene ring or an indoline ring substituted on the nitrogen atom by R$^{18}$, where R$^{18}$ is SO$_2$R$^{19}$ and R$^{19}$ is C$_{1-6}$alkyl.

10. A pharmaceutical composition comprising a compound as claimed in claim 1 or a pharmaceutically acceptable salt thereof in association with a pharmaceutically acceptable carrier or excipient.

11. A method for the treatment of physiological disorders selected from the group consisting of: pain, inflammation, migraine, emesis and postherpetic neuralgia, which method comprises administration to a patient in need thereof of a tachykinin reducing amount of a compound according to claim 1, or a pharmaceutically acceptable salt thereof, or a composition comprising a compound according to claim 1, or a pharmaceutically acceptable salt thereof.

12. A compound selected from:

3-(3,5-bis(trifluoromethyl)phenethyl)-4-benzyl-1-(3-(4,4'-indenylpiperidino)propyl)-5-oxo-1,2,4-triazole;

3-(3,5-bis(trifluoromethyl)phenethyl)-4-benzyl-1-(3-(4,4'-(N-sulfonamidomethylindolinyl)piperidino)propyl)-5-oxo-1,2,4-triazole;

3-(3,5-bis(trifluoromethyl)phenethyl)-4-benzyl-1-(3-(4,4'-(3,3'-indanyl)piperidinopropyl)-5-oxo-1,2,4-triazole;

or a pharmaceutically acceptable acid addition salt thereof.

* * * * *